April 14, 1936. P. DOT Plant Pat. 174
ROSE
Filed Oct. 18, 1935
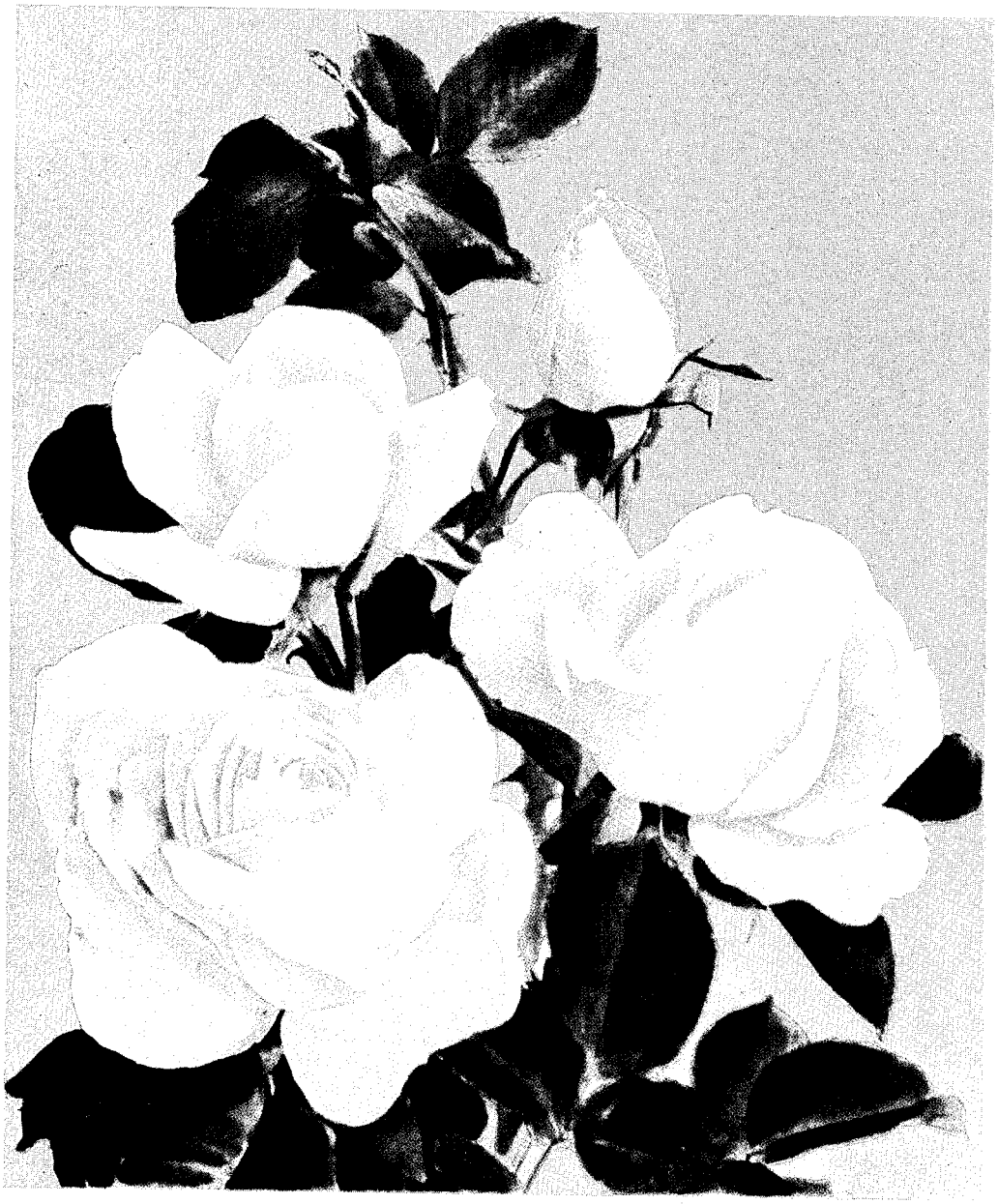
Inventor
Pedro Dot
By Robb & Robb
attorneys Patented Apr. 14, 1936 Plant Pat. 174

UNITED STATES PATENT OFFICE

174

ROSE

Pedro Dot, St. Feliu de Llobregat, Spain, assignor to The Conard-Pyle Company, West Grove, Pa.

Application October 18, 1935, Serial No. 45,671

1 Claim. (Cl. 47—61)

The present invention relates to a new and distinct variety of rose plant, the result of a definite breeding in an effort to produce a new color in garden roses.

This result was accomplished by crossing the Pernetiana Hybrid Roses "Duquesa de Penaranda" and "Magdalena de Nubiola." The former of these two known varieties is a close growing upright plant with flowers of a cinnamon peach color while the latter variety is a low growing plant of poor habit with flowers of warm salmon.

The new variety markedly differs from both parents in that the mutant or seedling plant is upright and branching and has flowers of scarlet red and rose doree with a burnt shade.

The novel characteristics of this new rose have been found to be fixed by asexual reproduction both in Spain and in the United States.

The following is a detailed description of the new variety as found in the test fields at West Grove, Pennsylvania, all reference to color herein according with Ridgway's Color Standard:—

Parentage:

*Seed parent.*—Duquesa de Penaranda.

*Pollen parent.*—Magdalena de Nubiola.

Classification:

Hybrid Pernetiana.

*Flower*

Blooming habit:

Continuous.

Bud:

*Size.*—Large.

*Form.*—Ovoid, pointed.

*Color.*—From nopal red at base to rose doree at edges, heavily veined carmine.

*Sepals.*—Branched with foliate ends, stand out straight.

*Calyx.*—Quite wide and deep, goblet shaped, smooth, fruit fragrance when rubbed.

*Peduncle.*—Short strong, reddish light green, covered with setæ.

*Opening.*—Opens well, does not ball.

Bloom:

*Size.*—4½ to 5 inches.

*Borne.*—Singly.

*Stems.*—Medium length, strong.

*Form.*—High centre, loose form when fully open, 3 or 4 petaloids covering the stamens.

*Permanence.*—Lasts well.

*Petalage.*—About 45.

*Color.*—As it opens face of the petals is scarlet red, reverse rose doree, heavily veined carmine; there is also a "burnt" shade which is not in the color chart. The color changes when fully open to eosine pink covered with a luminous sheen; there is a deep yellow base to each petal.

Petals:

*Texture.*—Thick leathery petals.

*Appearance.*—Inside satiny, outside metallic.

*Form.*—Pear shaped to round.

*Arrangement.*—Loosely formed.

*Persistence.*—Drop off cleanly.

*Fragrance.*—Strong, ripe blackberry.

*Lasting quality.*—Fragrance lasts and flower holds its form without wilting until petals fall.

Genital organs:

*Stamens, Anthers.*—Less than average number. Color—yellow. Arrangement—uneven.

*Stamens, Filaments (threads).* — Various lengths. Color—Yellow.

*Pollen.*—Yellow.

*Styles.* — Bunched, uneven length, slender, about even with stamens.

*Stigmas.*—Flesh colored.

*Ovaries.*—Normal.

Fruit:

Variety fertile with own pollen.

*Form.*—Bowl shaped, as broad as deep, globular.

*Aspect.*—Smooth.

*Color at maturity.*—Orange.

*Sepals.*—Fold back against the stem.

*Plant*

Form:

Bush.

Growth.

Upright, vigorous branching.

Foliage:

Number leaflets to compound leaf—3 on new foliage or in tips of shoots near flowers. 5 on mature or farther down.

*Size.*—Medium.

*Quantity.*—Abundant.

*Color.*—New foliage—pale green tinged with bronze at edges on both sides. Mature foliage—upper side medium green. Under side light green.

*Shape.*—Ovoid pointed, tip leaflet very broad.

*Texture.*—Leathery. Upper side smooth, shiny. Under side rough.

*Edge.*—Serrated.

*Serration.*—Even, not deep.

*Ribs and veins.*—Ordinary.

*Rachis.*—Color green, underside prickly.

*Stipules.*—Long, medium width, pointed, serrated.

*Disease resistance.*—Healthier than average

Pernetiana hybrid, but is subject to black spot.

Wood:

*New wood.*—Color light green with a slight reddish tinge, smooth.

*Old wood.*—Same.

Thorns:

*Quantity.*—Numerous.

*Form.*—Slightly hooked, broad base with tip opposite base of thorn.

*Color when young.*—Pink.

*Position.*—Irregular.

*Prickles.*—Scattered on some canes, missing on others.

*Short needles.*—Numerous on some canes, missing on others.

I claim:—

A new and distinct variety of rose plant as shown and described, characterized by the novelty of color of its fragrant flowers through all stages of their development.

PEDRO DOT.